(12) United States Patent
Ghosh et al.

(10) Patent No.: US 12,043,631 B2
(45) Date of Patent: Jul. 23, 2024

(54) BACE1 INHIBITORS FOR THE TREATMENT OF ALZHEIMER'S DISEASE

(71) Applicant: Purdue Research Foundation, West Lafayette, IN (US)

(72) Inventors: Arun K. Ghosh, West Lafayette, IN (US); Andrew Mesecar, West Lafayette, IN (US); Margherita Brindisi, Corleto Perticara (IT); Emilio Leal Cardenas, West Lafayette, IN (US)

(73) Assignee: Purdue Research Foundation

( * ) Notice: Subject to any disclaimer, the term of this patent is extended or adjusted under 35 U.S.C. 154(b) by 41 days.

(21) Appl. No.: 17/567,737

(22) Filed: Jan. 3, 2022

(65) Prior Publication Data

US 2022/0389030 A1 Dec. 8, 2022

Related U.S. Application Data

(62) Division of application No. 16/847,398, filed as application No. PCT/US2018/055655 on Oct. 12, 2018, now Pat. No. 11,214,579.

(60) Provisional application No. 62/572,088, filed on Oct. 13, 2017.

(51) Int. Cl.
| | |
|---|---|
| *C07D 307/22* | (2006.01) |
| *A61K 31/166* | (2006.01) |
| *A61K 31/341* | (2006.01) |
| *A61K 31/351* | (2006.01) |
| *A61P 25/28* | (2006.01) |
| *C07C 233/78* | (2006.01) |
| *C07D 309/14* | (2006.01) |
| *C07D 513/04* | (2006.01) |
| *C07D 513/06* | (2006.01) |
| *C07D 519/00* | (2006.01) |

(52) U.S. Cl.
CPC .......... *C07D 513/04* (2013.01); *C07C 233/78* (2013.01); *C07D 307/22* (2013.01); *C07D 309/14* (2013.01); *C07D 519/00* (2013.01)

(58) Field of Classification Search
CPC .. C07D 307/22; C07D 309/14; C07D 513/04; C07D 513/06; C07C 233/78; A61K 31/166; A61K 31/341; A61K 31/351; A61P 25/28
See application file for complete search history.

(56) References Cited

U.S. PATENT DOCUMENTS

| 2006/0229302 A1 | 10/2006 | Demont et al. |
| 2007/0073060 A1 | 3/2007 | Demont et al. |
| 2020/0299308 A1 | 9/2020 | Ghosh et al. |

FOREIGN PATENT DOCUMENTS

| WO | WO-2017066742 A1 | 4/2017 |
| WO | WO-2019075358 A1 | 4/2019 |

OTHER PUBLICATIONS

"U.S. Appl. No. 16/847,398, Final Office Action mailed Sep. 17, 2021", 7 pgs.
"U.S. Appl. No. 16/847,398, Non Final Office Action mailed Apr. 30, 2021", 11 pgs.
"U.S. Appl. No. 16/847,398, Notice of Allowance mailed Nov. 16, 2021", 10 pgs.
"U.S. Appl. No. 16/847,398, Response filed Apr. 15, 2021 to Restriction Requirement mailed Mar. 8, 2021", 21 pgs.
"U.S. Appl. No. 16/847,398, Response filed Jul. 27, 2021 to Non Final Office Action mailed Apr. 30, 2021", 22 pgs.
"U.S. Appl. No. 16/847,398, Response filed Nov. 3, 2021 to Final Office Action mailed Sep. 17, 2021", 19 pgs.
"U.S. Appl. No. 16/847,398, Restriction Requirement mailed Mar. 8, 2021", 7 pgs.
"CAPLUS printout of RN 1186648-17-8", (2009).
"CAPLUS printout of RN 1349211-27-3", (2011).
"International Application Serial No. PCT/US2018/055655, International Preliminary Report on Patentability mailed Feb. 24, 2020", 12 pgs.
"International Application Serial No. PCT/US2018/055655, International Search Report mailed Jan. 24, 2019", 4 pgs.
"International Application Serial No. PCT/US2018/055655, Invitation to Pay Additional Fees and Partial Search Report mailed Nov. 19, 2018", 2 pgs.
"International Application Serial No. PCT/US2018/055655, Written Opinion mailed Jan. 24, 2019", 7 pgs.
Ghosh, et al., "Design, Synthesis, and X-ray Structural Studies of BACE-1 Inhibitors Containing Substituted 2-Oxopiperazines as P1'-P2' Ligands", Bioorganic & Medicinal Chemistry Letters, vol. 27, No. 11, (2017), 2432-2438.
Ghosh, AK, et al., "Developing beta-secreatse inhibitors for treatment of Alzheimer's disease", Journal of Neurochemistry, vol. 12, Suppl. 1, (2012), 71-83.
Huang, et al., "Comprehensive 3D-QSAR and Binding Mode of BACE-1 Inhibitors Using R-group Search and Molecular Docking", Journal of Molecular Graphics and Modelling, vol. 45, (2013), 65-83.

*Primary Examiner* — Brenda L Coleman
(74) *Attorney, Agent, or Firm* — Schwegman Lundberg & Woessner, P.A.

(57) ABSTRACT

Described herein are compounds of the formulae (I)-(III) as well as pharmaceutical compositions comprising such compounds and methods for using such compounds/pharmaceutical compositions for treating Alzheimer's disease.

10 Claims, No Drawings

BACE1 INHIBITORS FOR THE TREATMENT OF ALZHEIMER'S DISEASE

CROSS-REFERENCE TO RELATED APPLICATIONS

This application is a divisional of U.S. patent application Ser. No. 16/847,398, filed Apr. 13, 2020, which is a U.S. National Stage Filing under 35 U.S.C. 371 from International Application No. PCT/US2018/055655, filed 12 Oct. 2018 and published as WO 2019/075358 A1 on 18 Apr. 2019, which claims the benefit of U.S. Provisional Appl. No. 62/572,088, filed Oct. 13, 2017; all of which are incorporated by reference as if fully set forth herein.

STATEMENT OF U.S. GOVERNMENT SUPPORT

This invention was made with government support under AG018933 awarded by the National Institutes of Health. The government has certain rights in the invention.

BACKGROUND

Memapsin 1 is a close homolog of memapsin 2, or beta-secretase (BACE), whose effect on beta-amyloid precursor protein (APP) leads to the production of beta-amyloid (A beta) peptide. BACE has been shown to play a role in the progression of Alzheimer's disease.

Alzheimer's disease is a progressive, degenerative disorder that attacks the brain's nerve cells, or neurons, resulting in loss of memory, thinking and language skills, and behavioral changes. Alzheimer's disease accounts for the majority of senile dementias and is a leading cause of death in adults. Anderson, R. N., *Natl. Vital Stat. Rep.* 49:1-87 (2001). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid peptide (Aβ) in the brain. Aβ accumulation plays a role in the pathogenesis and progression of the disease and is a proteolytic fragment of amyloid precursor protein (APP). Selkoe, D. J., *Nature* 399: 23-31 (1999). APP is cleaved initially by β-secretase followed by γ-secretase to generate Aβ. Lin, X., et al., *Proc. Natl. Acad. Sci. USA* 97:1456-1460 (2000); and De Stropper, B., et al., *Nature* 391:387-390 (1998).

Because of the large impact of Alzheimer's disease on the world's population and the apparent paucity of therapeutic agents that treat the disease by targeting (e.g., inhibiting) BACE1, there is a need for compounds designed for inhibiting the enzyme.

DESCRIPTION

Reference will now be made in detail to certain examples of the disclosed subject matter. While the disclosed subject matter will be described in conjunction with the enumerated claims, it will be understood that the exemplified subject matter is not intended to limit the claims to the disclosed subject matter.

Embodiments of this disclosure are directed to compounds of the general formula (I):

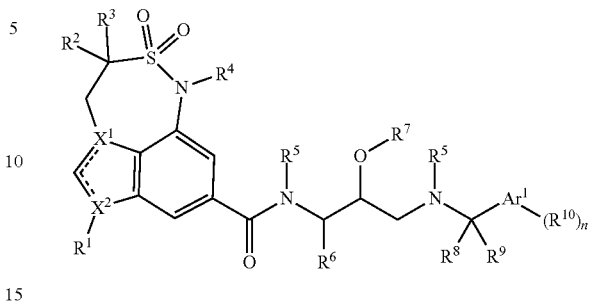

or a pharmaceutically acceptable salt, polymorph, prodrug, solvate or clathrate thereof,
wherein:
$X^1$ and $X^2$ are each, independently, N or C and the segmented lines represent a single or a double bond, with the proviso that one of the segmented lines represents a double bond;
$R^1$, $R^4$, and $R^7$ are each, independently, H or alkyl;
each $R^5$ is, independently, H or alkyl;
$R^2$ and $R^3$ are each, independently, hydrogen or alkyl or $R^2$ and $R^3$ together with the carbon atom to which they are attached, form a cycloalkyl group;
$R^6$ is alkyl, alkylaryl or arylalkyl;
$R^8$ and $R^9$ are each, independently, H or a heterocyclyl group, or $R^9$, together with $R^8$ and the carbon atom to which $R^9$ is attached, forms a cycloalkyl group or a heterocyclyl group; and
$Ar^1$ is aryl or heteroaryl;
n is an integer from 0-3; and
$R^{10}$ is H, halo, alkyl, alkoxy, nitro or $NR^aR^b$, wherein $R^a$ and $R^b$ are each, independently, H or alkyl or $R^a$ and $R^b$, together with the nitrogen atom to which they are attached, form an aryl group or a heterocyclyl group or $R^{10}$ and $R^9$, together with any intervening atoms, form a heterocyclyl group.

The compound of the formula (I) can be a compound of the formula (Ia) or (Ib):

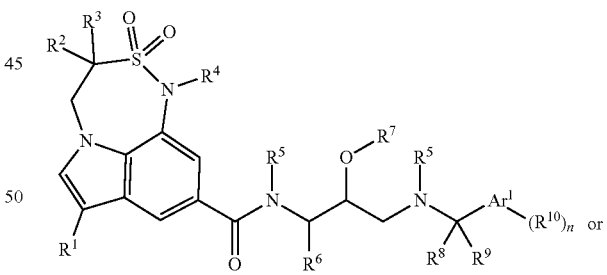

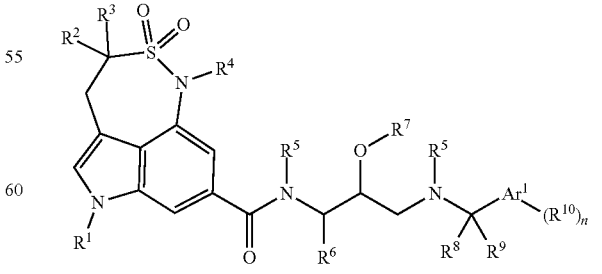

or a pharmaceutically acceptable salt, polymorph, prodrug, solvate or clathrate thereof, wherein $R^1$-$R^{10}$ are defined herein.

The compound of the formula (I) can also be a compound of the formula (Ic) or (Id):

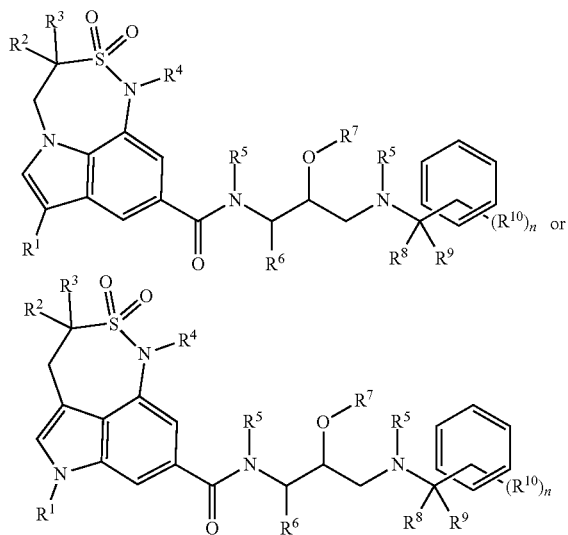

or a pharmaceutically acceptable salt, polymorph, prodrug, solvate or clathrate thereof, wherein $R^1$-$R^{10}$ are defined herein.

Embodiments of this disclosure are also directed to compounds of the general formula (II):

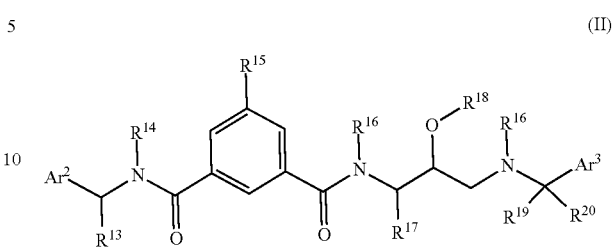

(II)

or a pharmaceutically acceptable salt, polymorph, prodrug, solvate or clathrate thereof, wherein:

$Ar^2$ and $Ar^3$ are each independently aryl;

$R^{13}$ is hydrogen, alkyl or arylalkyl;

$R^{14}$ and $R^{16}$ are each, independently, hydrogen or alkyl;

$R^{15}$ is hydrogen, alkyl or —$NR^{21}_2$ (wherein each $R^{21}$ is, independently, hydrogen, alkyl or —$SO_2R^{22}$, wherein $R^{22}$ is hydrogen or alkyl);

$R^{17}$ is arylalkyl; and $R^{19}$ and $R^{20}$, together with the carbon atom to which they are attached, form a cycloalkyl or a heterocyclyl group.

Compounds contemplated herein include compounds of the formula:

| Compound | Structure |
|---|---|
| 1 | 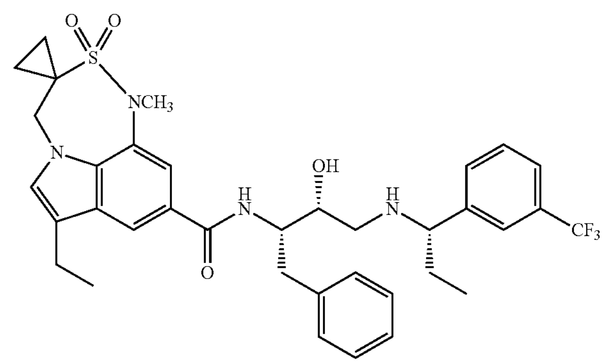 [SMILES: CCc1cn2c3c(cc(C(=O)N[C@@H](Cc4ccccc4)[C@H](O)CN[C@@H](CC)c4cccc(C(F)(F)F)c4)cc13)N(C)S(=O)(=O)C1(CC1)C2] |
| 2 | 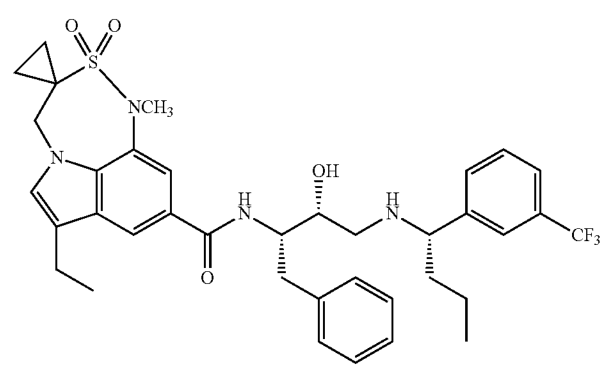 [SMILES: CCC[C@H](NC[C@@H](O)[C@H](Cc1ccccc1)NC(=O)c1cc2c3c(c1)c(CC)cn3CC1(CC1)S(=O)(=O)N2C)c1cccc(C(F)(F)F)c1] |

-continued

| Compound | Structure |
|---|---|
| 3 | 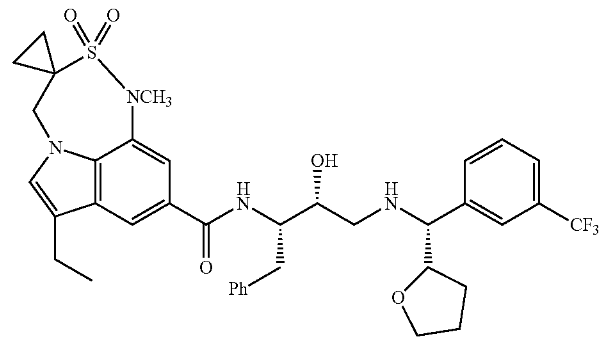 [SMILES: CCc1cn2c3c(cc(C(=O)N[C@@H](Cc4ccccc4)[C@H](O)CN[C@H](c4cccc(C(F)(F)F)c4)C4CCCO4)cc13)N(C)S(=O)(=O)C1(CC1)C2] |
| 4 | 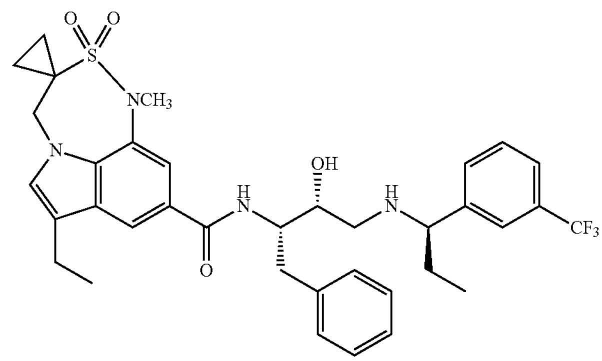 [SMILES: CCc1cn2c3c(cc(C(=O)N[C@@H](Cc4ccccc4)[C@H](O)CN[C@H](CC)c4cccc(C(F)(F)F)c4)cc13)N(C)S(=O)(=O)C1(CC1)C2] |
| 5 | 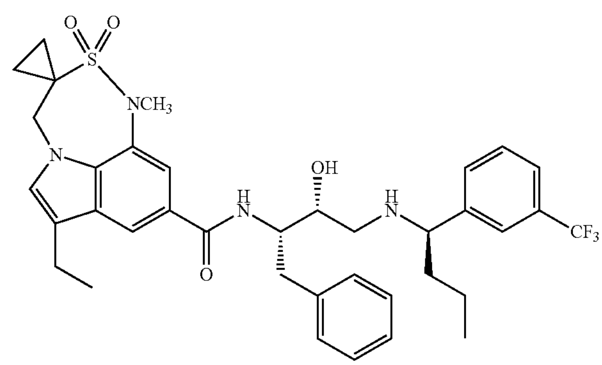 [SMILES: CCC[C@@H](NC[C@@H](O)[C@H](Cc1ccccc1)NC(=O)c1cc2c3c(c1)c(CC)cn3CC1(CC1)S(=O)(=O)N2C)c1cccc(C(F)(F)F)c1] |
| 6 | 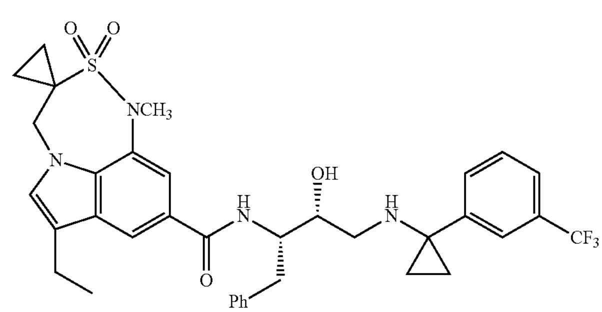 [SMILES: CCc1cn2c3c(cc(C(=O)N[C@@H](Cc4ccccc4)[C@H](O)CNC4(c5cccc(C(F)(F)F)c5)CC4)cc13)N(C)S(=O)(=O)C1(CC1)C2] |

-continued
| Compound | Structure |
|---|---|
| 7 | 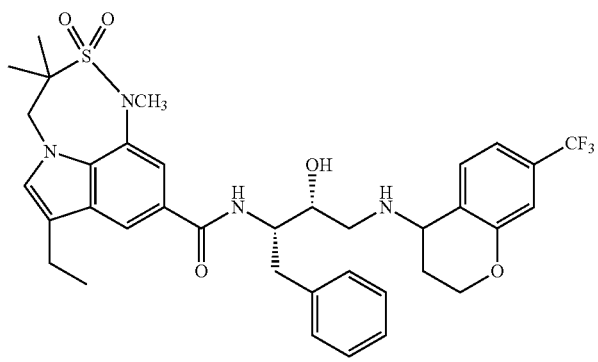 [SMILES: CCc1cn2c3c(cc(C(=O)N[C@@H](Cc4ccccc4)[C@H](O)CNC4CCOc5cc(C(F)(F)F)ccc54)cc13)N(C)S(=O)(=O)C(C)(C)C2] |
| 8 | 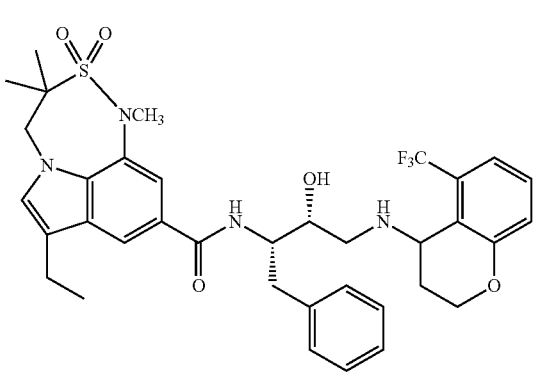 [SMILES: CCc1cn2c3c(cc(C(=O)N[C@@H](Cc4ccccc4)[C@H](O)CNC4CCOc5cccc(C(F)(F)F)c54)cc13)N(C)S(=O)(=O)C(C)(C)C2] |
| 9 | 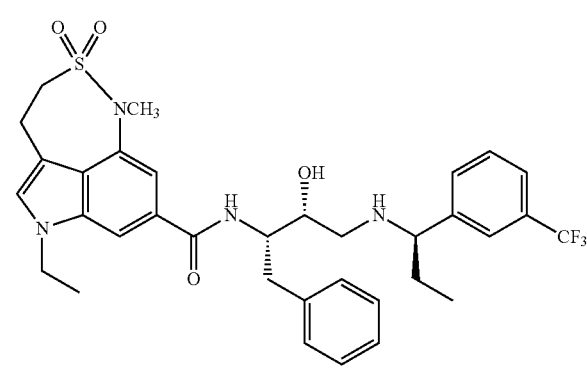 [SMILES: CC[C@@H](NC[C@@H](O)[C@H](Cc1ccccc1)NC(=O)c1cc2c3c(cn(CC)c3c1)CCS(=O)(=O)N2C)c1cccc(C(F)(F)F)c1] |
| 10 | 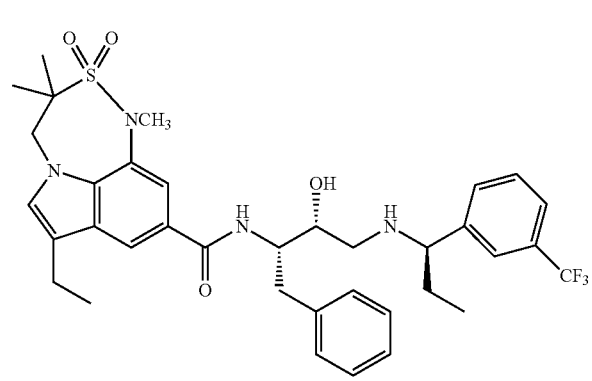 [SMILES: CCc1cn2c3c(cc(C(=O)N[C@@H](Cc4ccccc4)[C@H](O)CN[C@H](CC)c4cccc(C(F)(F)F)c4)cc13)N(C)S(=O)(=O)C(C)(C)C2] |

-continued

| Compound | Structure |
|---|---|
| 11 | 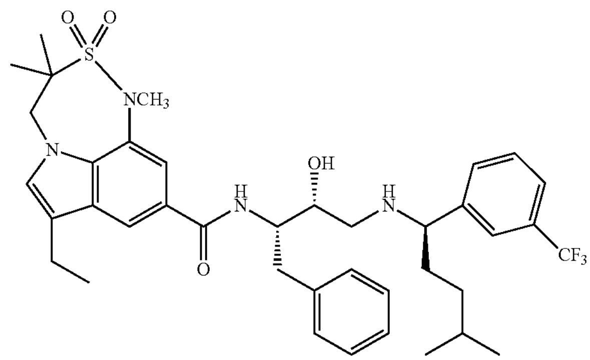 [SMILES: CCc1cn2c3c(cc(C(=O)N[C@@H](Cc4ccccc4)[C@H](O)CN[C@H](CCC(C)C)c4cccc(C(F)(F)F)c4)cc13)N(C)S(=O)(=O)C(C)(C)C2] |
| 12 | |
| 13 | 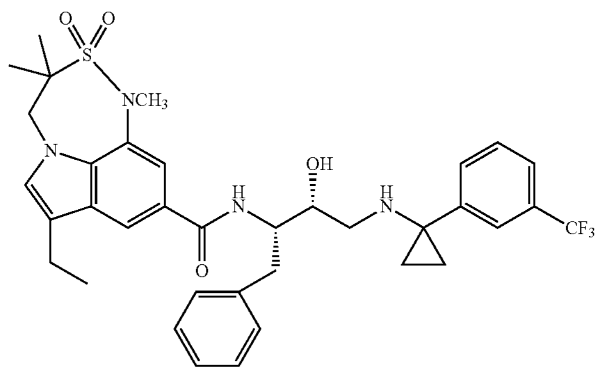 [SMILES: CCc1cn2c3c(cc(C(=O)N[C@@H](Cc4ccccc4)[C@H](O)CNC4(c5cccc(C(F)(F)F)c5)CC4)cc13)N(C)S(=O)(=O)C(C)(C)C2] |
| 14 | 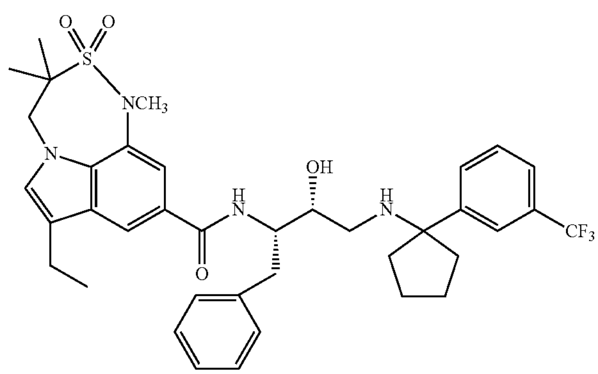 [SMILES: CCc1cn2c3c(cc(C(=O)N[C@@H](Cc4ccccc4)[C@H](O)CNC4(c5cccc(C(F)(F)F)c5)CCCC4)cc13)N(C)S(=O)(=O)C(C)(C)C2] |
| 15 | 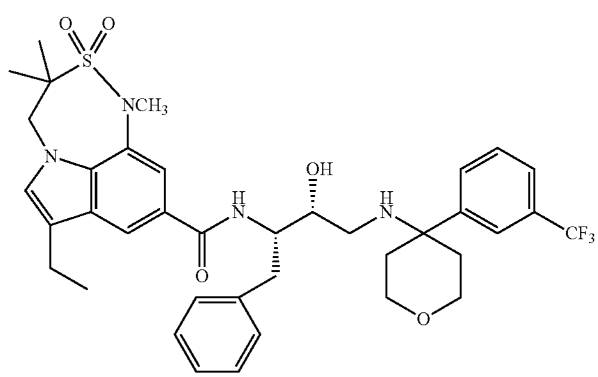 [SMILES: CCc1cn2c3c(cc(C(=O)N[C@@H](Cc4ccccc4)[C@H](O)CNC4(c5cccc(C(F)(F)F)c5)CCOCC4)cc13)N(C)S(=O)(=O)C(C)(C)C2] |

-continued
| Compound | Structure |
|---|---|
| 16 | 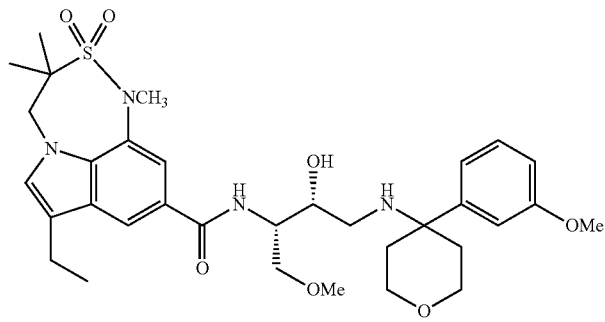 [SMILES: CCc1cn2c3c(cc(C(=O)N[C@@H](COC)[C@H](O)CNC4(c5cccc(OC)c5)CCOCC4)cc13)N(C)S(=O)(=O)C(C)(C)C2] |
| 17 | 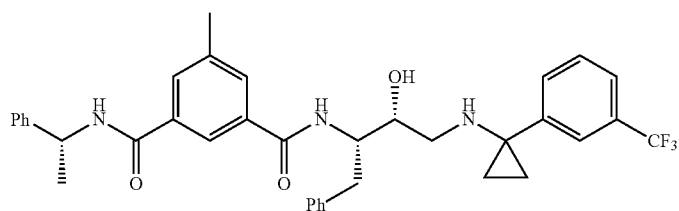 [SMILES: Cc1cc(C(=O)N[C@@H](Cc2ccccc2)[C@H](O)CNC2(c3cccc(C(F)(F)F)c3)CC2)cc(C(=O)N[C@H](C)c2ccccc2)c1] |
| 18 | 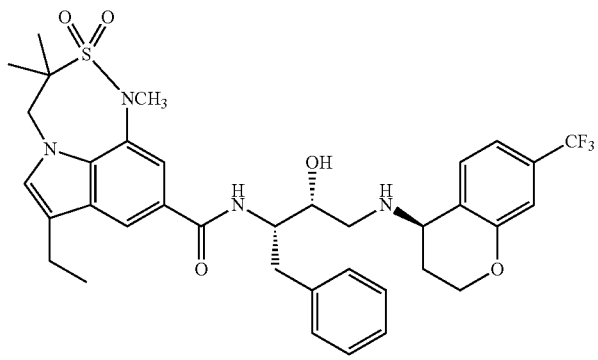 [SMILES: CCc1cn2c3c(cc(C(=O)N[C@@H](Cc4ccccc4)[C@H](O)CN[C@@H]4CCOc5cc(C(F)(F)F)ccc54)cc13)N(C)S(=O)(=O)C(C)(C)C2] |
| 19 | 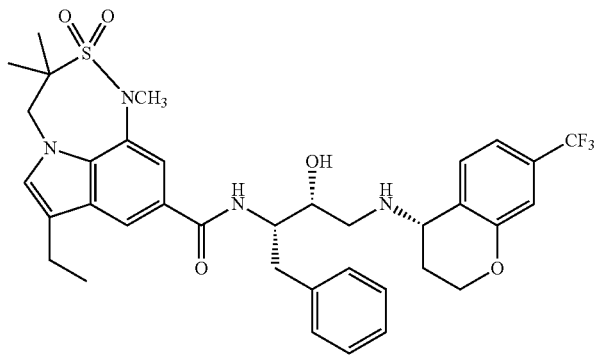 [SMILES: CCc1cn2c3c(cc(C(=O)N[C@@H](Cc4ccccc4)[C@H](O)CN[C@H]4CCOc5cc(C(F)(F)F)ccc54)cc13)N(C)S(=O)(=O)C(C)(C)C2] |

-continued

| Compound | Structure |
|---|---|
| 20 | *(chemical structure)* |
| 21 | *(chemical structure)* |
| 22 | *(chemical structure)* |
| 23 | *(chemical structure)* |

-continued

| Compound | Structure |
|---|---|
| 24 | 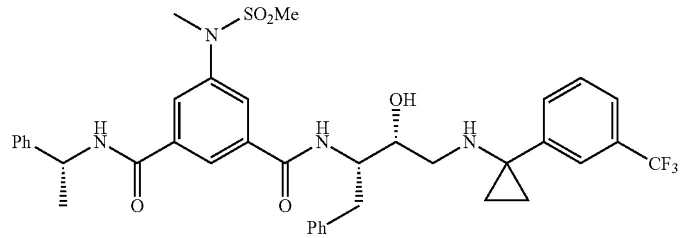 [SMILES: C[C@@H](NC(=O)c1cc(C(=O)N[C@@H](Cc2ccccc2)[C@H](O)CNC2(c3cccc(C(F)(F)F)c3)CC2)cc(N(C)S(C)(=O)=O)c1)c1ccccc1] |
| 25 | 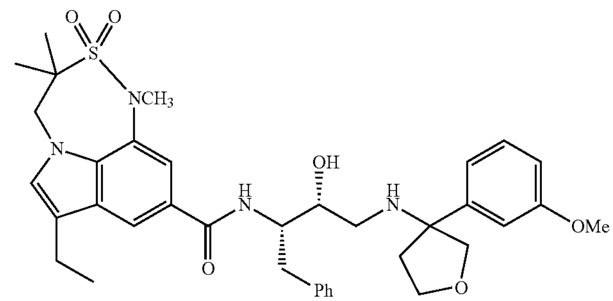 [SMILES: CCc1cn2c3c(cc(C(=O)N[C@@H](Cc4ccccc4)[C@H](O)CNC4(c5cccc(OC)c5)CCOC4)cc13)N(C)S(=O)(=O)C(C)(C)C2] |
| 26 | 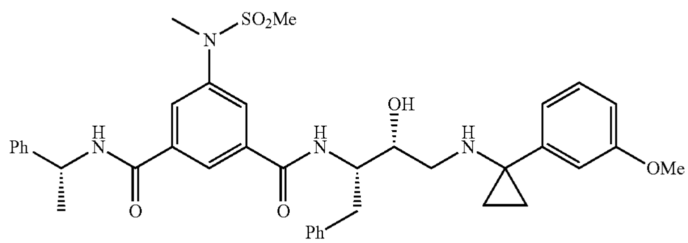 [SMILES: COc1cccc(C2(NC[C@@H](O)[C@H](Cc3ccccc3)NC(=O)c3cc(C(=O)N[C@H](C)c4ccccc4)cc(N(C)S(C)(=O)=O)c3)CC2)c1] |
| 27 | 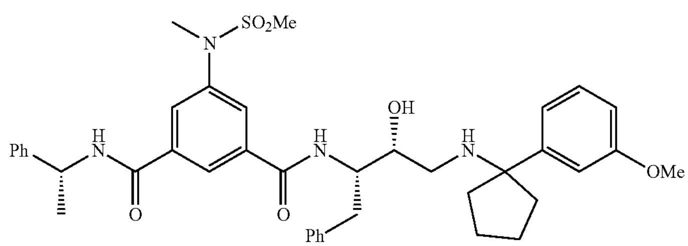 [SMILES: COc1cccc(C2(NC[C@@H](O)[C@H](Cc3ccccc3)NC(=O)c3cc(C(=O)N[C@H](C)c4ccccc4)cc(N(C)S(C)(=O)=O)c3)CCCC2)c1] |
| 28 | 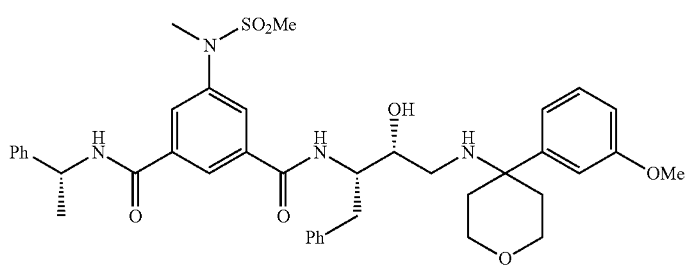 [SMILES: COc1cccc(C2(NC[C@@H](O)[C@H](Cc3ccccc3)NC(=O)c3cc(C(=O)N[C@H](C)c4ccccc4)cc(N(C)S(C)(=O)=O)c3)CCOCC2)c1] |
| 29 | 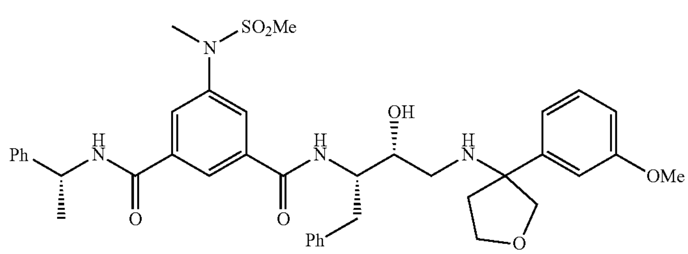 [SMILES: COc1cccc(C2(NC[C@@H](O)[C@H](Cc3ccccc3)NC(=O)c3cc(C(=O)N[C@H](C)c4ccccc4)cc(N(C)S(C)(=O)=O)c3)CCOC2)c1] |

| Compound | Structure |
|---|---|
| 30 | 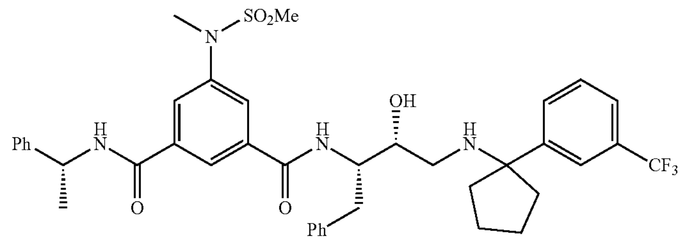 [SMILES: C[C@@H](NC(=O)c1cc(C(=O)N[C@@H](Cc2ccccc2)[C@H](O)CNC2(c3cccc(C(F)(F)F)c3)CCCC2)cc(N(C)S(C)(=O)=O)c1)c1ccccc1] |
| 31 | 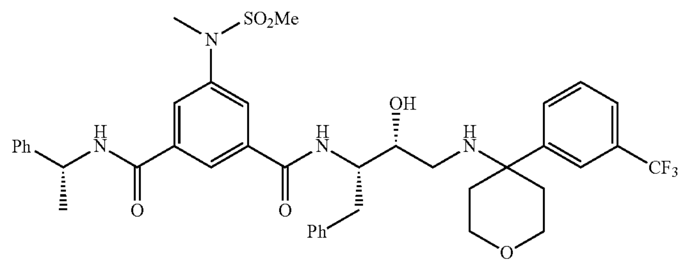 [SMILES: C[C@@H](NC(=O)c1cc(C(=O)N[C@@H](Cc2ccccc2)[C@H](O)CNC2(c3cccc(C(F)(F)F)c3)CCOCC2)cc(N(C)S(C)(=O)=O)c1)c1ccccc1] |
| 32 | 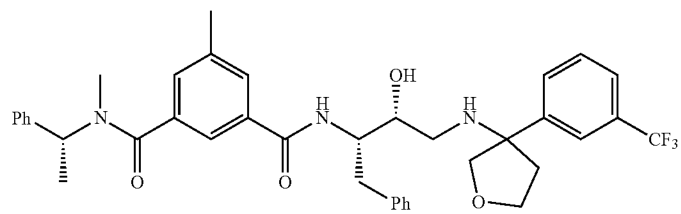 [SMILES: Cc1cc(C(=O)N[C@@H](Cc2ccccc2)[C@H](O)CNC2(c3cccc(C(F)(F)F)c3)CCOC2)cc(C(=O)N(C)[C@H](C)c2ccccc2)c1] |
| 33 | 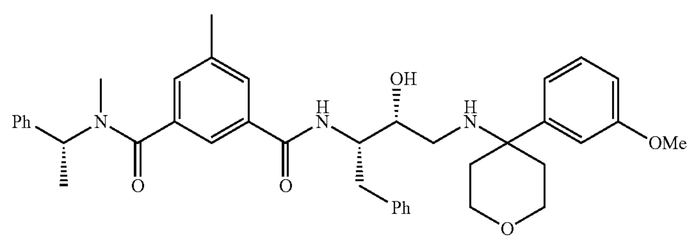 [SMILES: COc1cccc(C2(NC[C@@H](O)[C@H](Cc3ccccc3)NC(=O)c3cc(C)cc(C(=O)N(C)[C@H](C)c4ccccc4)c3)CCOCC2)c1] |
| 34 | 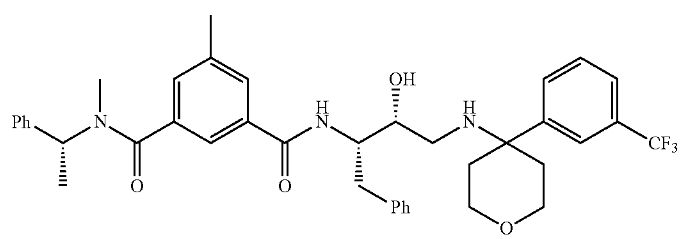 [SMILES: Cc1cc(C(=O)N[C@@H](Cc2ccccc2)[C@H](O)CNC2(c3cccc(C(F)(F)F)c3)CCOCC2)cc(C(=O)N(C)[C@H](C)c2ccccc2)c1] |
| 35 | 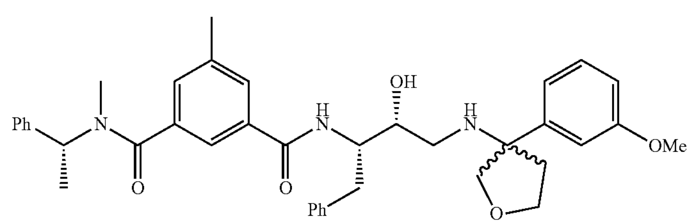 |

-continued

| Compound | Structure |
|---|---|
| 36 | 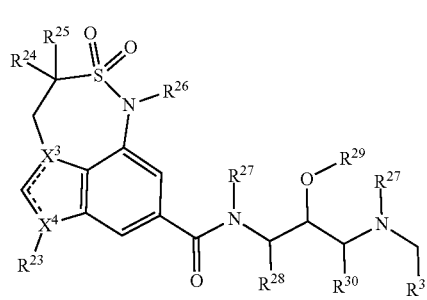 |
| 37 | 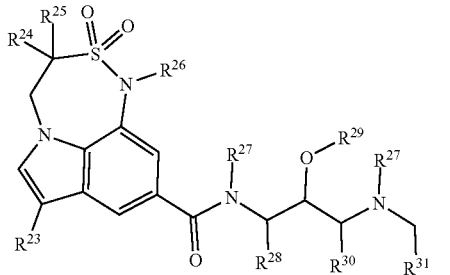 |

Embodiments of this disclosure are directed to compounds of the general formula (III):

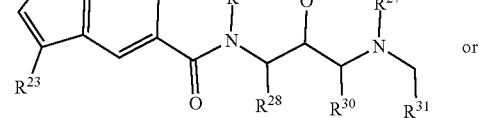

(III)

or a pharmaceutically acceptable salt, polymorph, prodrug, solvate or clathrate thereof,
wherein:
$X^3$ and $X^4$ are each, independently, N or C and the segmented lines represent a single or a double bond, with the proviso that one of the segmented lines represents a double bond;
$R^{23}$, $R^{26}$, and $R^{29}$ are each, independently, H or alkyl;
each $R^{27}$ is, independently, H or alkyl;
$R^{24}$ and $R^{25}$ are each, independently, hydrogen or alkyl or $R^{24}$ and $R^{25}$ together with the carbon atom to which they are attached, form a cycloalkyl group;
$R^{28}$ is alkyl or arylalkyl; and
$R^{30}$ and $R^{31}$, together with the carbon atoms to which they are attached, form a heterocyclyl group (e.g., a five- or six-membered heterocyclyl group or a five- or six-membered heterocyclyl group containing at least two nitrogen atoms in the ring).

Embodiments of this disclosure are also directed to compounds of the general formula (IIIa) and (IIIb):

(IIIa)

(IIIb)

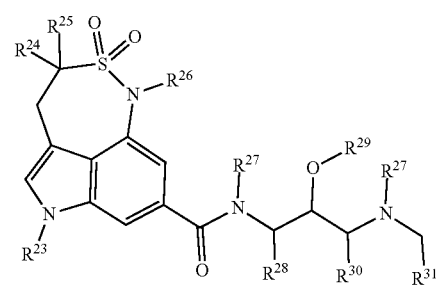

or a pharmaceutically acceptable salt, polymorph, prodrug, solvate or clathrate thereof, wherein $R^{23}$-$R^{31}$ are defined herein.

For example, the compound of the formula (III) can be a compound of the formula (IIIc):

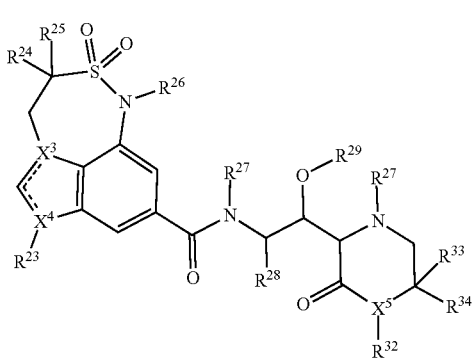

(IIIc)

or a pharmaceutically acceptable salt, polymorph, prodrug, solvate or clathrate thereof, wherein $X^3$, $X^4$, and $R^{23}$-$R^{29}$ are defined herein; $X^5$ is CH or N; $R^{32}$ is hydrogen, acyl, alkyl, arylalkyl or —SO$_2$R$^{35}$, wherein $R^{35}$ is hydrogen or alkyl; and $R^{33}$ and $R^{34}$ are each, independently, H, alkyl, and halo or $R^{34}$, together with $R^{32}$, form a heterocyclyl group.

In one example, the compound of the formula (IIIc) can be a compound of the formula (IIId) and (IIIe):

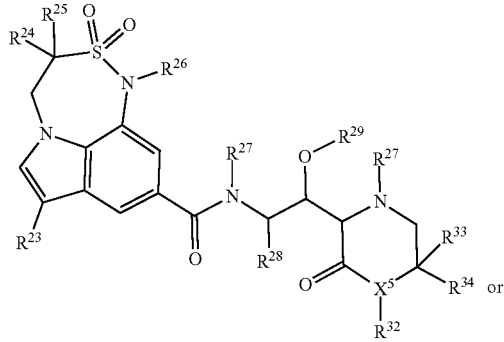

(IIId)

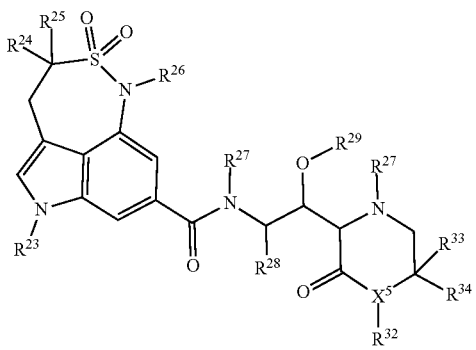

(IIIe)

or a pharmaceutically acceptable salt, polymorph, prodrug, solvate or clathrate thereof, wherein $X^3$, $X^4$, $X^5$, $R^{23}$-$R^{29}$, $R^{32}$, $R^{33}$, and $R^{34}$ are defined herein.

Embodiments of this disclosure are also directed to compounds of the general formula (IIIf):

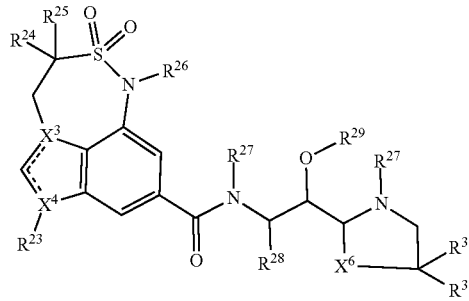

(IIIf)

or a pharmaceutically acceptable salt, polymorph, prodrug, solvate or clathrate thereof, wherein $X^3$, $X^4$, and $R^{23}$-$R^{29}$ are defined herein; $R^{35}$ and $R^{36}$ are each, independently, halo, alkoxy, aryloxy, heterocyclyloxy, or —SO$_2$R$^{37}$, wherein $R^{37}$ is hydrogen or alkyl; and $X^6$ is CHCR$^{38}$ or CH$_2$CHR$^{38}$, wherein $R^{38}$ is hydrogen or alkyl.

Embodiments of this disclosure are also directed to compounds of the general formula (IIIg):

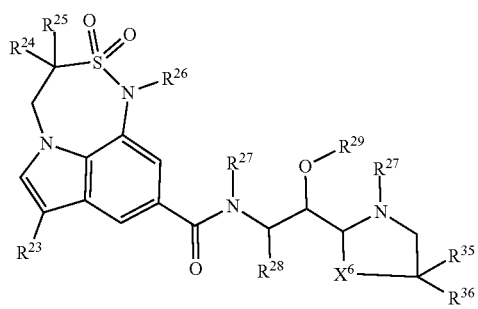

(IIIg)

or a pharmaceutically acceptable salt, polymorph, prodrug, solvate or clathrate thereof, wherein $R^{23}$-$R^{29}$ are defined herein; $R^{35}$ and $R^{36}$ are each, independently, halo, alkoxy, aryloxy, heterocyclyloxy, or —SO$_2$R$^{37}$, wherein $R^{37}$ is hydrogen or alkyl; and $X^6$ is CHCR$^{38}$ or CH$_2$CHR$^{38}$, wherein $R^{38}$ is hydrogen or alkyl.

Embodiments of this disclosure are also directed to compounds of the general formula (IIIh):

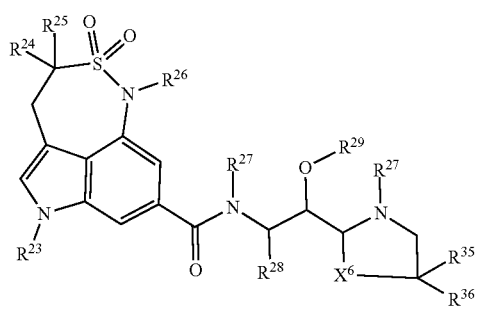

(IIIh)

or a pharmaceutically acceptable salt, polymorph, prodrug, solvate or clathrate thereof, wherein $R^{23}$-$R^{29}$ are defined herein; $R^{35}$ and $R^{36}$ are each, independently, halo, alkoxy, aryloxy, heterocyclyloxy, or —$SO_2R^{37}$, wherein $R^{37}$ is hydrogen or alkyl; and $X^6$ is $CHCR^{38}$ or $CH_2CHR^{38}$, wherein $R^{38}$ is hydrogen or alkyl.

Compounds contemplated herein include compounds of the formula:

| Compound | Structure |
|---|---|
| 38 | 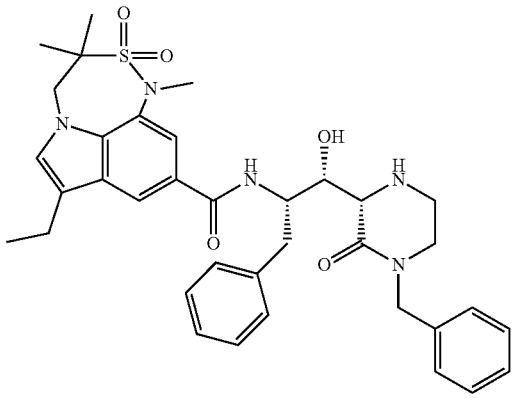 [SMILES: CCc1cn2c3c(cc(C(=O)N[C@@H](Cc4ccccc4)[C@H](O)[C@@H]4NCCN(Cc5ccccc5)C4=O)cc13)N(C)S(=O)(=O)C(C)(C)C2] |
| 39 | 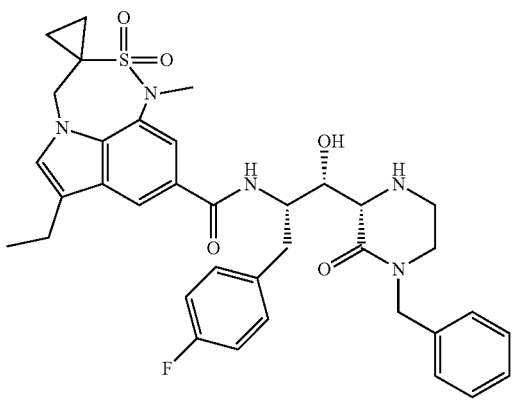 [SMILES: CCc1cn2c3c(cc(C(=O)N[C@@H](Cc4ccc(F)cc4)[C@H](O)[C@@H]4NCCN(Cc5ccccc5)C4=O)cc13)N(C)S(=O)(=O)C1(CC1)C2] |
| 40 | 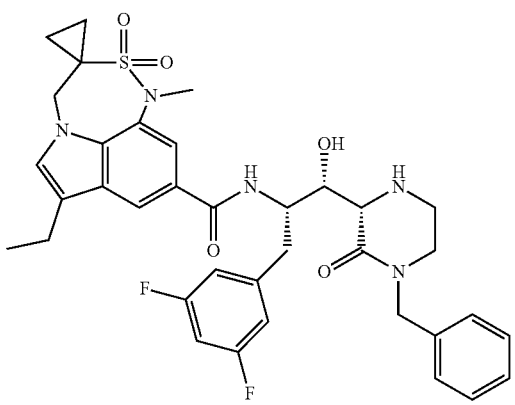 [SMILES: CCc1cn2c3c(cc(C(=O)N[C@@H](Cc4cc(F)cc(F)c4)[C@H](O)[C@@H]4NCCN(Cc5ccccc5)C4=O)cc13)N(C)S(=O)(=O)C1(CC1)C2] |

-continued

| Compound | Structure |
|---|---|
| 41 | 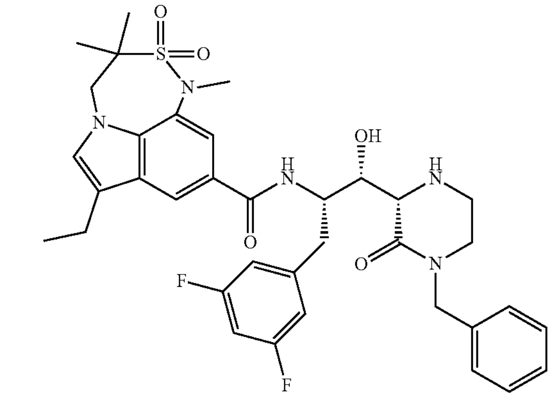 [SMILES: CCc1cn2c3c(cc(C(=O)N[C@@H](Cc4cc(F)cc(F)c4)[C@H](O)[C@@H]4NCCN(Cc5ccccc5)C4=O)cc13)N(C)S(=O)(=O)C(C)(C)C2] |
| 42 | 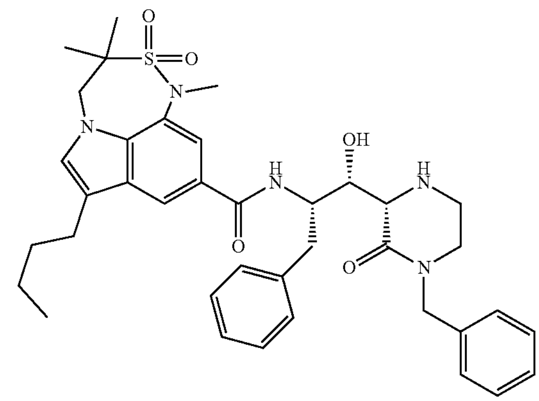 [SMILES: CCCCc1cn2c3c(cc(C(=O)N[C@@H](Cc4ccccc4)[C@H](O)[C@@H]4NCCN(Cc5ccccc5)C4=O)cc13)N(C)S(=O)(=O)C(C)(C)C2] |
| 43 | 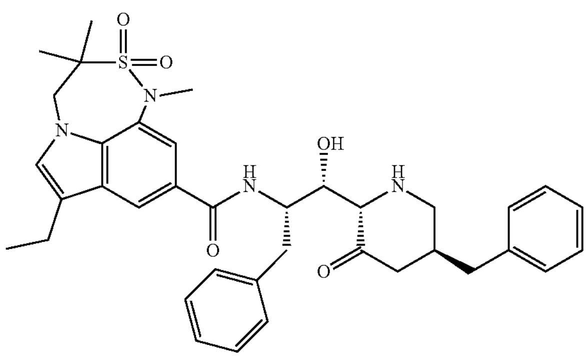 [SMILES: CCc1cn2c3c(cc(C(=O)N[C@@H](Cc4ccccc4)[C@H](O)[C@@H]4NC[C@@H](Cc5ccccc5)CC4=O)cc13)N(C)S(=O)(=O)C(C)(C)C2] |
| 44 | 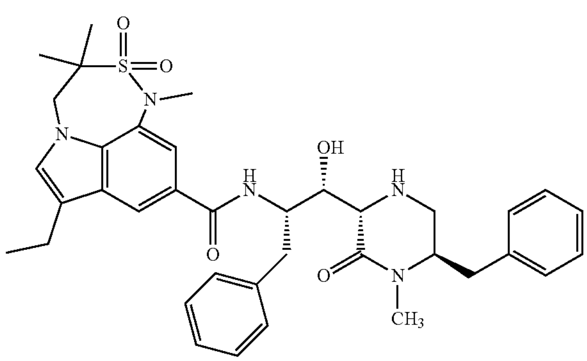 [SMILES: CCc1cn2c3c(cc(C(=O)N[C@@H](Cc4ccccc4)[C@H](O)[C@@H]4NC[C@@H](Cc5ccccc5)N(C)C4=O)cc13)N(C)S(=O)(=O)C(C)(C)C2] |

-continued

| Compound | Structure |
|---|---|
| 45 | 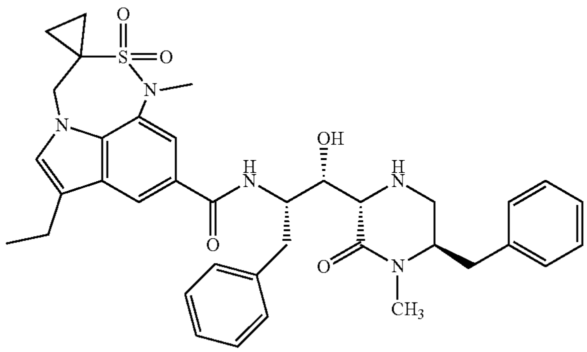 [SMILES: CCc1cn2c3c(cc(C(=O)N[C@@H](Cc4ccccc4)[C@H](O)[C@@H]4NC[C@@H](Cc5ccccc5)N(C)C4=O)cc13)N(C)S(=O)(=O)C1(CC1)C2] |
| 46 | 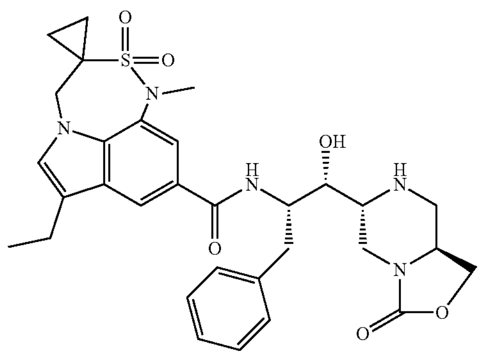 [SMILES: CCc1cn2c3c(cc(C(=O)N[C@@H](Cc4ccccc4)[C@H](O)[C@H]4CN5C(=O)OC[C@@H]5CN4)cc13)N(C)S(=O)(=O)C1(CC1)C2] |
| 47 | 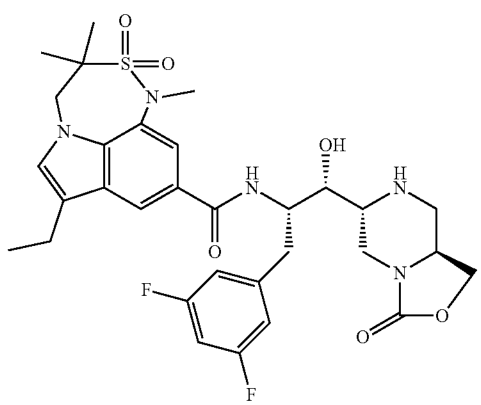 [SMILES: CCc1cn2c3c(cc(C(=O)N[C@@H](Cc4cc(F)cc(F)c4)[C@H](O)[C@H]4CN5C(=O)OC[C@@H]5CN4)cc13)N(C)S(=O)(=O)C(C)(C)C2] |
| 48 | 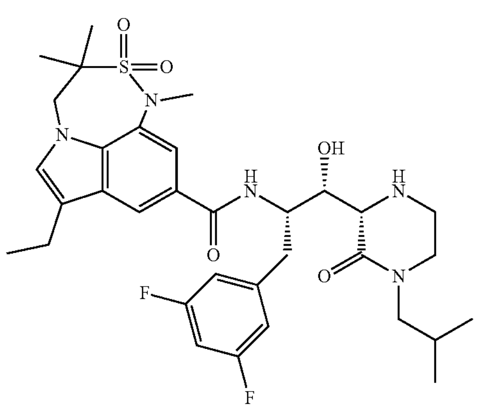 [SMILES: CCc1cn2c3c(cc(C(=O)N[C@@H](Cc4cc(F)cc(F)c4)[C@H](O)[C@@H]4NCCN(CC(C)C)C4=O)cc13)N(C)S(=O)(=O)C(C)(C)C2] |

-continued

| Compound | Structure |
|---|---|
| 50 | 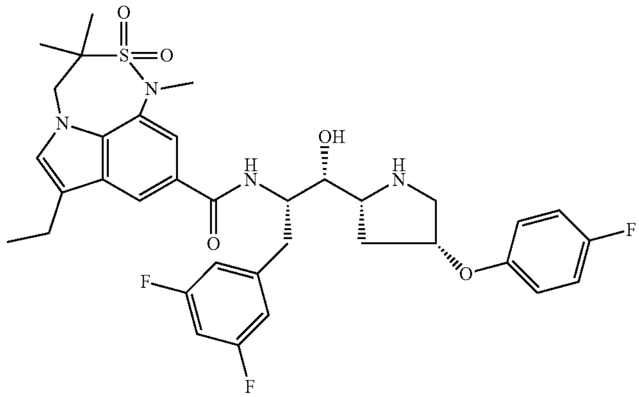 [SMILES: CCc1cn2c3c(cc(C(=O)N[C@@H](Cc4cc(F)cc(F)c4)[C@H](O)[C@H]4C[C@@H](Oc5ccc(F)cc5)CN4)cc13)N(C)S(=O)(=O)C(C)(C)C2] |
| 51 | 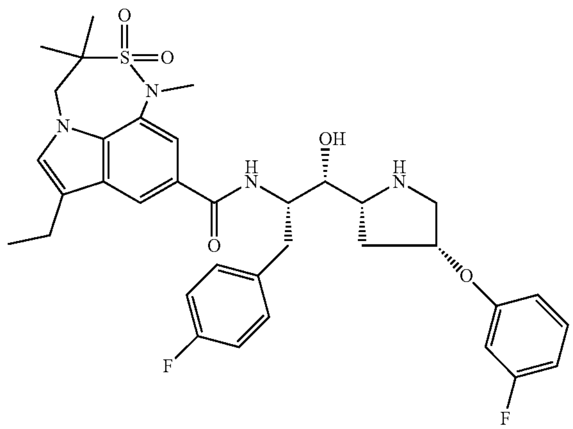 [SMILES: CCc1cn2c3c(cc(C(=O)N[C@@H](Cc4ccc(F)cc4)[C@H](O)[C@H]4C[C@@H](Oc5cccc(F)c5)CN4)cc13)N(C)S(=O)(=O)C(C)(C)C2] |
| 52 | 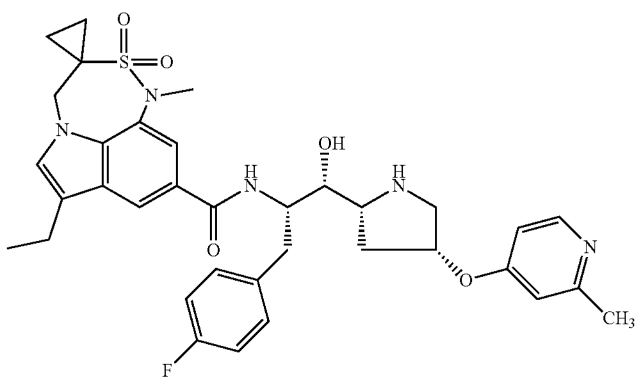 [SMILES: CCc1cn2c3c(cc(C(=O)N[C@@H](Cc4ccc(F)cc4)[C@H](O)[C@H]4C[C@@H](Oc5ccnc(C)c5)CN4)cc13)N(C)S(=O)(=O)C1(CC1)C2] |
| 53 | 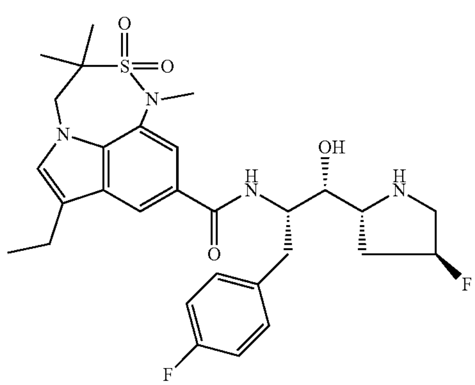 [SMILES: CCc1cn2c3c(cc(C(=O)N[C@@H](Cc4ccc(F)cc4)[C@H](O)[C@H]4C[C@H](F)CN4)cc13)N(C)S(=O)(=O)C(C)(C)C2] |

-continued

| Compound | Structure |
|---|---|
| 54 | 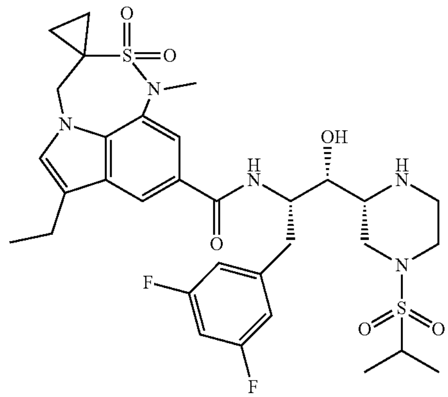 [SMILES: CCc1cn2c3c(cc(C(=O)N[C@@H](Cc4cc(F)cc(F)c4)[C@H](O)[C@H]4CN(S(=O)(=O)C(C)C)CCN4)cc13)N(C)S(=O)(=O)C1(CC1)C2] |
| 55 | 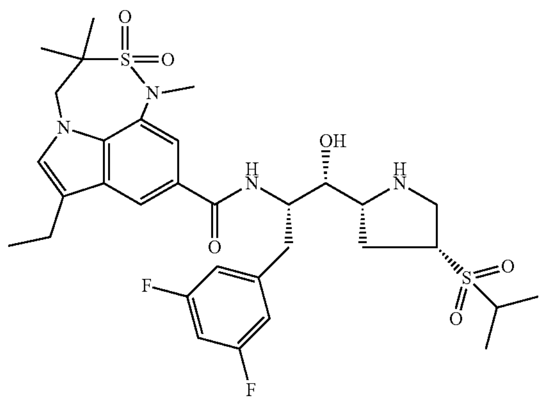 [SMILES: CCc1cn2c3c(cc(C(=O)N[C@@H](Cc4cc(F)cc(F)c4)[C@H](O)[C@H]4C[C@@H](S(=O)(=O)C(C)C)CN4)cc13)N(C)S(=O)(=O)C(C)(C)C2] |
| 56 | 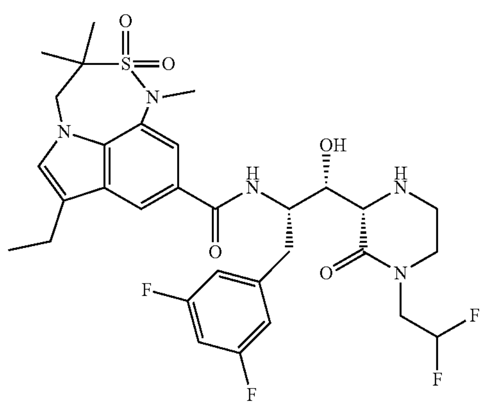 [SMILES: CCc1cn2c3c(cc(C(=O)N[C@@H](Cc4cc(F)cc(F)c4)[C@H](O)[C@@H]4NCCN(CC(F)F)C4=O)cc13)N(C)S(=O)(=O)C(C)(C)C2] |
| 57 | 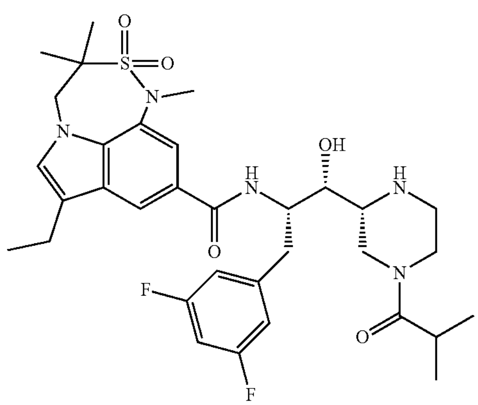 [SMILES: CCc1cn2c3c(cc(C(=O)N[C@@H](Cc4cc(F)cc(F)c4)[C@H](O)[C@H]4CN(C(=O)C(C)C)CCN4)cc13)N(C)S(=O)(=O)C(C)(C)C2] |

| Compound | Structure |
|---|---|
| 58 | 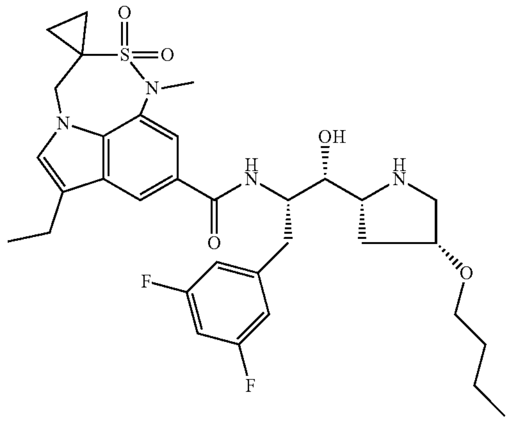 [SMILES: CCCCO[C@H]1CN[C@@H]([C@@H](O)[C@H](Cc2cc(F)cc(F)c2)NC(=O)c2cc3c4c(c2)c(CC)cn4CC2(CC2)S(=O)(=O)N3C)C1] |
| 59 | 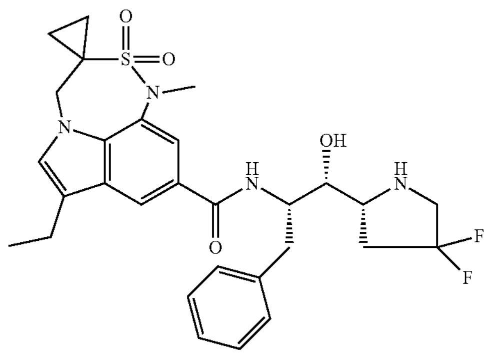 [SMILES: CCc1cn2c3c(cc(C(=O)N[C@@H](Cc4ccccc4)[C@H](O)[C@H]4CC(F)(F)CN4)cc13)N(C)S(=O)(=O)C1(CC1)C2] |

Those of ordinary skill in the art will recognize that the compounds described herein can contain chiral centers. All diastereomers of the compounds described herein are contemplated herein, as well as racemates. Prodrugs of the compounds described are also contemplated herein.

Various examples contemplate pharmaceutical compositions comprising one or more compounds of the various embodiments described herein and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice Of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one example, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions contemplated herein. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. Pharmaceutical compositions can be orally administered as a capsule (hard or soft), tablet (film coated, enteric coated or uncoated), powder or granules (coated or uncoated) or liquid (solution or suspension). Formulations can be conveniently prepared by any of the methods well-known in the art. Pharmaceutical compositions can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited examples, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound can vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms can be dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds described herein or an appropriate pharmaceutical composition thereof are effective, the compounds can be administered in an effective amount. The dosages as suitable for the purposes of this disclosure can be a composition, a pharmaceutical composition or any other compositions described herein.

For each of the recited examples, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one example, the dosage may be administered daily for up to and including 30 days, preferably between 7-10 days. In another example, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, compositions contemplated herein can effect prophylaxis of recurring symptoms. For example, the dosage may be administered once or twice a day to prevent the onset of symptoms in patients at risk, especially for asymptomatic patients.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Pharmaceutical compositions comprising a therapeutically effective amount of one or more compounds described herein are contemplated. Also contemplated is the use of the compounds described herein as a medicament for treating a patient in need of relief from a disease or a condition, such as Alzheimer's disease. Other embodiments are directed to a method for treating a patient (e.g., a human patient) in need of relief from Alzheimer's disease, the method comprising the step of administering to the patient a therapeutically effective amount of a compound described herein or a pharmaceutical composition comprising a therapeutically effective amount of a compound described herein.

The term "therapeutically effective amount" as used herein, refers to that amount of one or more compounds described herein that elicits a biological or medicinal response in a tissue system, animal or human, that is being sought by a researcher, veterinarian, medical doctor or other clinician, which includes alleviation of the symptoms of the disease or disorder being treated. In some examples, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of this disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" as used herein refers to a group (e.g., alkyl, aryl, and heteroaryl) or molecule in which one or more hydrogen atoms contained thereon are replaced by one or more substituents. The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "alkyl" and "alkylene" as used herein refers to substituted or unsubstituted monovalent and divalent straight chain and branched alkyl and alkylene groups and cycloalkyl and cycloalkylene groups having from 1 to 40 carbon atoms (C$_1$-C$_{40}$), 1 to about 20 carbon atoms (C$_1$-C$_{20}$), 1 to 12 carbons (C$_1$-C$_{12}$), 1 to 8 carbon atoms (C$_1$-C$_8$), or, in some examples, from 1 to 6 carbon atoms (C$_1$-C$_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Examples of straight chain divalent alkylene groups include those with from 1 to 8 carbon atoms such as ethyl (—$CH_2CH_2$—), n-propyl (—$CH_2CH_2CH_2$—), n-butyl (—$CH_2CH_2CH_2CH_2$—), n-pentyl (—$CH_2CH_2CH_2CH_2CH_2$—), n-hexyl (—$CH_2CH_2CH_2CH_2CH_2CH_2$—), n-heptyl (—$CH_2CH_2CH_2CH_2CH_2CH_2CH_2$—), and n-octyl (—$CH_2CH_2CH_2CH_2CH_2CH_2CH_2CH_2$—) groups. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, cyclohexenyl, cyclopentenyl, cyclohexadienyl, butadienyl, pentadienyl, and hexadienyl among others.

As used herein, the term "hetero," as used, e.g., in the term "heterocyclyl," includes heteroatoms such as N, O, and S. In certain variations, illustrative heteroatoms also include phosphorus, and selenium.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some examples, the cycloalkyl group can have 3 to about 8-12 ring members, whereas in other examples the number of ring carbon atoms range from 3 to 4, 5, 6, or 7. In some examples, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some examples, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some examples, heterocyclyl groups include 3 to about 20 ring members, whereas other such groups have 3 to about 15 ring members. In some examples, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$), 3 to 4 carbon atoms ($C_3$-$C_4$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an example of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "alkenyloxy" as used herein refers to an oxygen atom connected to an alkenyl group.

The term "amine" as used herein refers to primary, secondary, and tertiary amines having, e.g., the formula N(group)₃ wherein each group can independently be H or non-H, such as alkyl, aryl, and the like. Amines include but are not limited to alkylamines, arylamines, arylalkylamines; dialkylamines, diarylamines, diaralkylamines, heterocyclylamines and the like; and ammonium ions.

The term "alkylamino" as used herein refers to N(group)₃ group, wherein one of the groups is an alkyl group.

The term "alkenylamino" as used herein refers to N(group)₃ group, wherein one of the groups is an alkenyl group.

The terms "halo," "halogen," or "halide" group, as used herein, by themselves or as part of another substituent, mean, unless otherwise stated, a fluorine, chlorine, bromine, or iodine atom.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound described herein. Examples of prodrugs include, but are not limited to, derivatives and metabolites of a compound including biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

What is claimed is:

1. A compound of the formula (II):

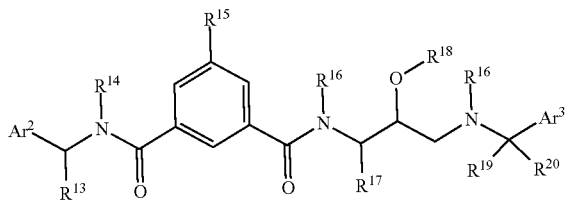

or a pharmaceutically acceptable salt or hydrate thereof, wherein:
$Ar^2$ and $Ar^3$ are each independently aryl;
$R^{13}$ is hydrogen, alkyl or arylalkyl;
$R^{14}$ and $R^{16}$ are each, independently, hydrogen or alkyl;
$R^{15}$ is alkyl and $R^{19}$ and $R^{20}$, together with the carbon atom to which they are attached, form a tetrahydrofuranyl or a tetrahydropyranyl group or
$R^{15}$ is $-NR^{21}_2$ (wherein each $R^{21}$ is, independently, hydrogen, alkyl or $-SO_2R^{22}$, wherein $R^{22}$ is hydrogen or alkyl) and $R^{19}$ and $R^{20}$, together with the carbon atom to which they are attached, form a cycloalkyl or a heterocyclyl group;
$R^{17}$ is arylalkyl; and
$R^{18}$ is H.

2. The compound of claim 1, wherein the compound is of the formula:

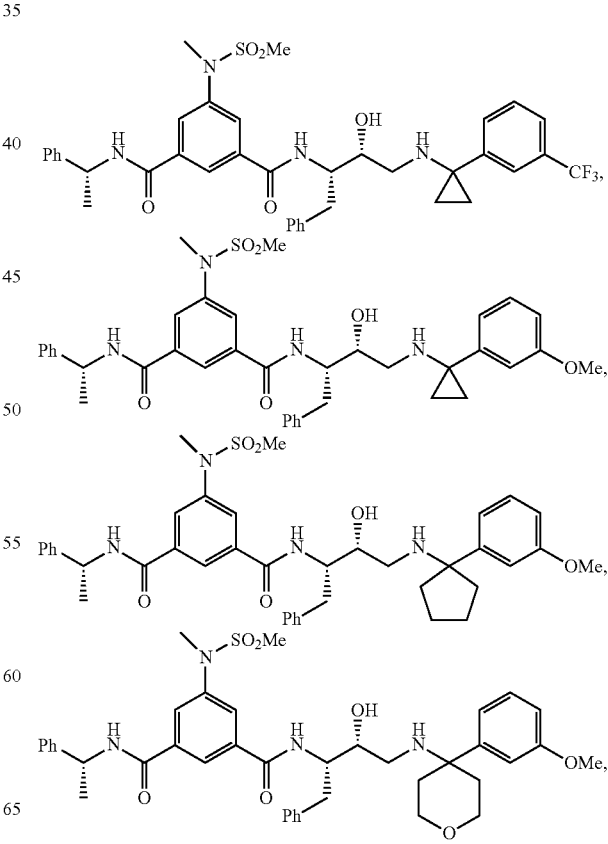

-continued

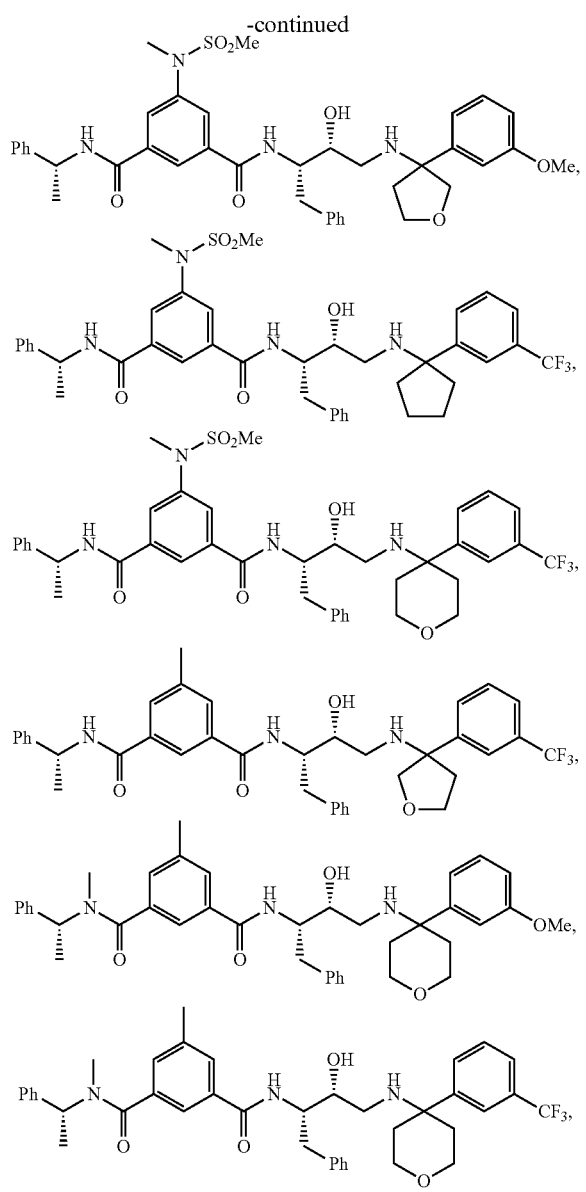

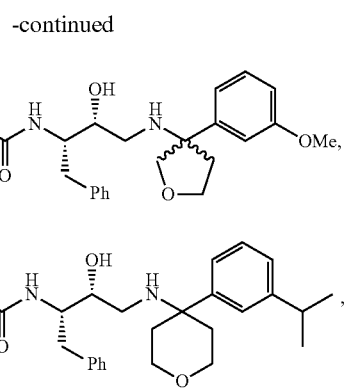

or a pharmaceutically acceptable salt or hydrate thereof.

3. A pharmaceutical composition comprising a compound of claim 1 or a pharmaceutically acceptable salt or hydrate thereof and a pharmaceutically acceptable excipient.

4. A method a method for treating a patient in need of relief from Alzheimer's disease, the method comprising the step of administering to the patient a therapeutically effective amount of a compound of claim 1 or a pharmaceutically acceptable salt or hydrate thereof.

5. The compound of claim 1 or a pharmaceutically acceptable salt or hydrate thereof, wherein $R^{13}$ is alkyl.

6. The compound of claim 1 or a pharmaceutically acceptable salt or hydrate thereof, wherein $R^{14}$ is alkyl.

7. The compound of claim 1 or a pharmaceutically acceptable salt or hydrate thereof, wherein $R^{15}$ is —$NR^{21}_2$, wherein each $R^{21}$ is, independently, hydrogen, alkyl or —$SO_2R^{22}$, wherein $R^{22}$ is hydrogen or alkyl.

8. The compound of claim 7 or a pharmaceutically acceptable salt or hydrate thereof, wherein one $R^{21}$ is alkyl and the other $R^{21}$ is —$SO_2R^{22}$, wherein $R^{22}$ is hydrogen or alkyl.

9. The compound of claim 8 or a pharmaceutically acceptable salt or hydrate thereof, wherein $R^{22}$ is alkyl.

10. The compound of claim 1 or a pharmaceutically acceptable salt or hydrate thereof, wherein $R^{17}$ is benzyl.

* * * * *